United States Patent [19]  
Jessup et al.

[11] 4,203,445  
[45] May 20, 1980

[54] GAS-VENTING FILTER ASSEMBLY FOR COLLECTION DEVICE

[75] Inventors: James L. Jessup, Elk Grove Village; Eugene W. Elliott, Barrington, both of Ill.

[73] Assignee: Hollister Incorporated, Chicago, Ill.

[21] Appl. No.: 968,445

[22] Filed: Dec. 11, 1978

[51] Int. Cl.$^2$ .............................................. A61F 5/44
[52] U.S. Cl. .................................................... 128/283
[58] Field of Search .............. 128/275, 276, 283, 286, 128/294, 295, DIG. 24

[56] References Cited

U.S. PATENT DOCUMENTS

| | | | |
|---|---|---|---|
| 3,439,677 | 4/1969 | Bonfils | 128/283 |
| 3,439,679 | 4/1969 | Doolittle | 128/283 |
| 3,575,170 | 4/1971 | Clark | 128/275 |
| 3,759,260 | 9/1973 | Nolan et al. | 128/283 |
| 3,804,091 | 4/1974 | Nolan et al. | 128/283 |
| 3,865,109 | 2/1975 | Elmore et al. | 128/283 |
| 3,952,727 | 4/1976 | Nolan | 128/283 |
| 3,998,255 | 12/1976 | Mather et al. | 128/275 |

Primary Examiner—Robert W. Michell  
Assistant Examiner—C. F. Rosenbaum  
Attorney, Agent, or Firm—Tilton, Fallon, Lungmus & Chestnut

[57] ABSTRACT

A gas-venting filter assembly for a collection device such as a colostomy pouch includes an outwardly extending recess in a wall of the pouch which is bridged by a filter unit that is designed for the free flow of gas therethrough. Preferably, the pouch recess is provided with an aperture in the form of a slit which provides suitable venting in normal use. Pressure build-up within the collection device resulting in ballooning of the device and/or discomfort to the wearer is avoided while at the same time protecting the filter assembly in use, and also facilitating leakage testing during manufacturing.

14 Claims, 6 Drawing Figures

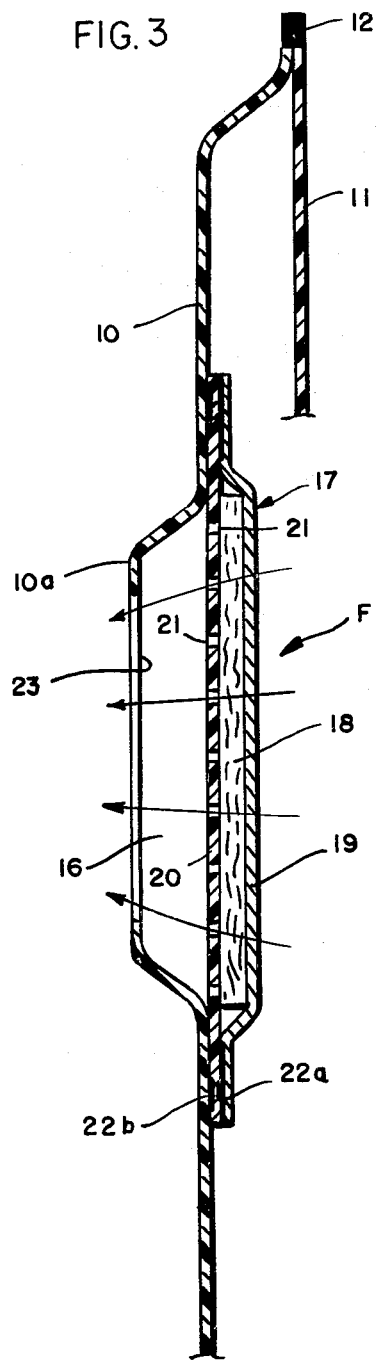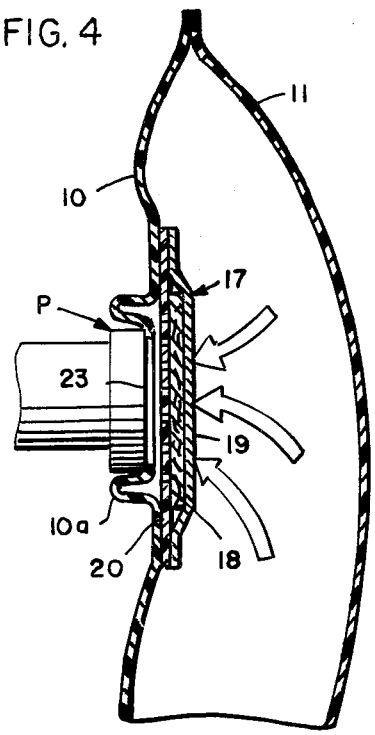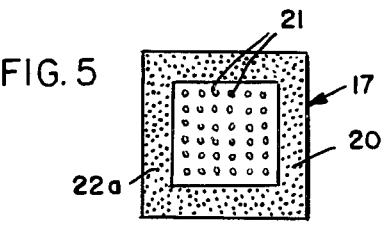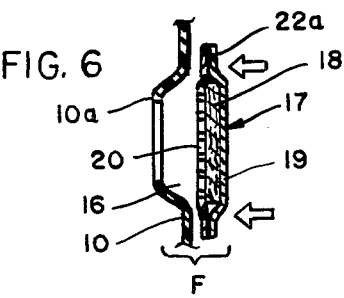

GAS-VENTING FILTER ASSEMBLY FOR COLLECTION DEVICE

BACKGROUND AND PRIOR ART

Stoma caps or covers, which are used with a colostomy stoma, have been provided with gas-venting filters. See, for example, U.S. Pat. No. 3,804,091. Such caps fit snugly over the stoma, and are not designed to receive large amounts of discharge. They are essentially protective covers, and usually include an absorbent pad for collecting a small amount of discharge. In accordance with prior design, as described in the cited patent, the gas is vented through the filter by a circuitous route to provide greater contact between the activated carbon of the filter and the vented gas. The resulting restriction in the rate of gas venting may cause a pressure build-up resulting in discomfort to the wearer, who may have to correct the condition by temporarily breaking the seal between the cap and the skin area surrounding the stoma.

It has been proposed to provide certain other kinds of collection devices, such as colostomy pouches, with gas-venting filters. Prior art devices of this type are described in U.S. Pat. Nos. 3,952,727 and 3,759,260. The filters of both of these patents also utilize an indirect or circuitous gas venting principle. This is accomplished, for example, by forcing the gas to enter the end of the filter cake, or by offsetting openings in the inner and outer covers of the filter cake. Colostomy devices equipped with such filter assemblies could therefore permit a build-up of pressure to occur within the pouch under conditions where large amounts of gas are being discharged from the stoma. This would cause the pouch to distend or "balloon". This is objectionable to the wearer because it makes the ostomy appliance more noticeable. Such "ballooning" of colostomy pouches is a recognized problem for the wearers of stoma pouches. To prevent such distension of the pouch, ostomates have resorted to expedients, such as making pinholes in the pouch, or temporarily breaking the seal of the pouch to the skin, thereby "burping" the pouch. Either practice is objectionable because of the release of unpleasant odors.

As will be apparent from the foregoing discussion, there has been a need for a gas-venting filter assembly which can be applied to collection appliances to preclude gas build-up and ballooning of the appliance while deodorizing the vented gas. With such a free venting filter, however, there may be a problem in the transmission of liquid from within the pouch. There is also a problem of protecting the filter assembly from external water if the appliance is worn while the ostomate is taking a shower.

Still another design problem is that the collection appliance should be capable of being tested for leakage during manufacture. The wearer needs assurance by such testing that the pouch is fully sealed and has no leaks through which liquid or gas can escape. The leakage testing has ordinarily been carried out by inflating the pouch, but where the pouch contains a free venting filter this is difficult to carry out.

SUMMARY OF INVENTION

This invention relates to a gas-venting filter assembly for use in combination with a collection appliance. The combination of the invention is particularly desirable for use with colostomy pouches, but it also has advantageous application to stoma caps which are used with colostomies and similar appliances. More broadly, the filter assembly of this invention may be used with any collection appliance with which continuous gas-venting is desirable, including drainable pouches, such as those used with ileostomy or urostomy stomas. Colostomy pouches which are capable of distension, but which are normally worn flat, can be prevented from ballooning by utilization of the gas-venting filter assembly of this invention. At the same time, the pouches can be readily tested for leakage after installation of the filter assembly. Moreover, in use the filter assembly is protected internally from the liquid discharge, and externally from the entry of foreign material. It is also shielded from water if worn while the ostomate is taking a shower.

The collection appliances include an envelope or enclosure, which may be of small size where the appliance is used as a stoma cap, or may be of larger size for stoma pouches designed to hold larger amounts of discharge. As conventionally fabricated, such stoma pouches or caps are formed of fluid and odor impermeable thermoplastic sheet material, including front and rear panels sealed together around their peripheries to provide the envelope or enclosure. The rear panel has an opening for receiving discharge, and attachment means is provided around the opening for forming a temporary seal to the skin of the wearer. The filter assembly of this invention is designed for use with appliances of this general construction.

As one of the novel elements of the combination of the present invention, a recess or depression is provided in a panel or wall of the pouch. The recess is on the interior or enclosed side of the panel, and the portion of the panel providing the recess is displaced outwardly from the plane of that panel. For cooperation with the recess, a generally flat or planar filter unit is arranged so that it bridges the recess with its peripheral portion extending onto and sealably connected to the inside of the panel around the recess. In general, the filter unit comprises a gas-porous cake containing activated carbon covered on its opposite sides by gas-porous sheet material so that gas from within the enclosure can flow freely through the filter unit. There is also provided a gas outlet aperture in the outwardly displaced panel portion, the aperture being of size and shape so as to be essentially nonflow-restricting with respect to the vented gas. Preferably, the aperture consists of a slit which tends to be self closing when the panel portion is untensioned. The slit should extend generally vertically and preferably has an S-shaped configuration. As will subsequently be explained in greater detail, the displaced panel portion is normally spaced from the one side of the filter unit. Such an arrangement facilitates leakage testing and provides a protective shield over the exterior of the filter while allowing free venting of gas in use. Internally, it is preferred that the cake of filtered material be enclosed by porous sheet material which has been treated so that it is repellent to the liquid discharge. Further constructional features and advantages will be described in the following detailed description.

THE DRAWINGS

The accompanying drawings illustrate a preferred embodiment of the invention as applied to a stoma pouch.

FIG. 3 is an enlarged fragmentary sectional view of the ostomy appliance and filter assembly combination, taken on line 3—3 of FIG. 1;

FIG. 4 is a fragmentary sectional view similar to FIG. 3, illustrating a procedure for leakage testing of the appliance;

FIG. 5 is a front or plan view of the filter unit prior to attachment to the front wall of the ostomy appliance; and FIG. 6 is a fragmentary sectional view illustrating the recess in the front panel of the appliance and the filter unit prior to assembly.

DETAILED DESCRIPTION

Figure 1:
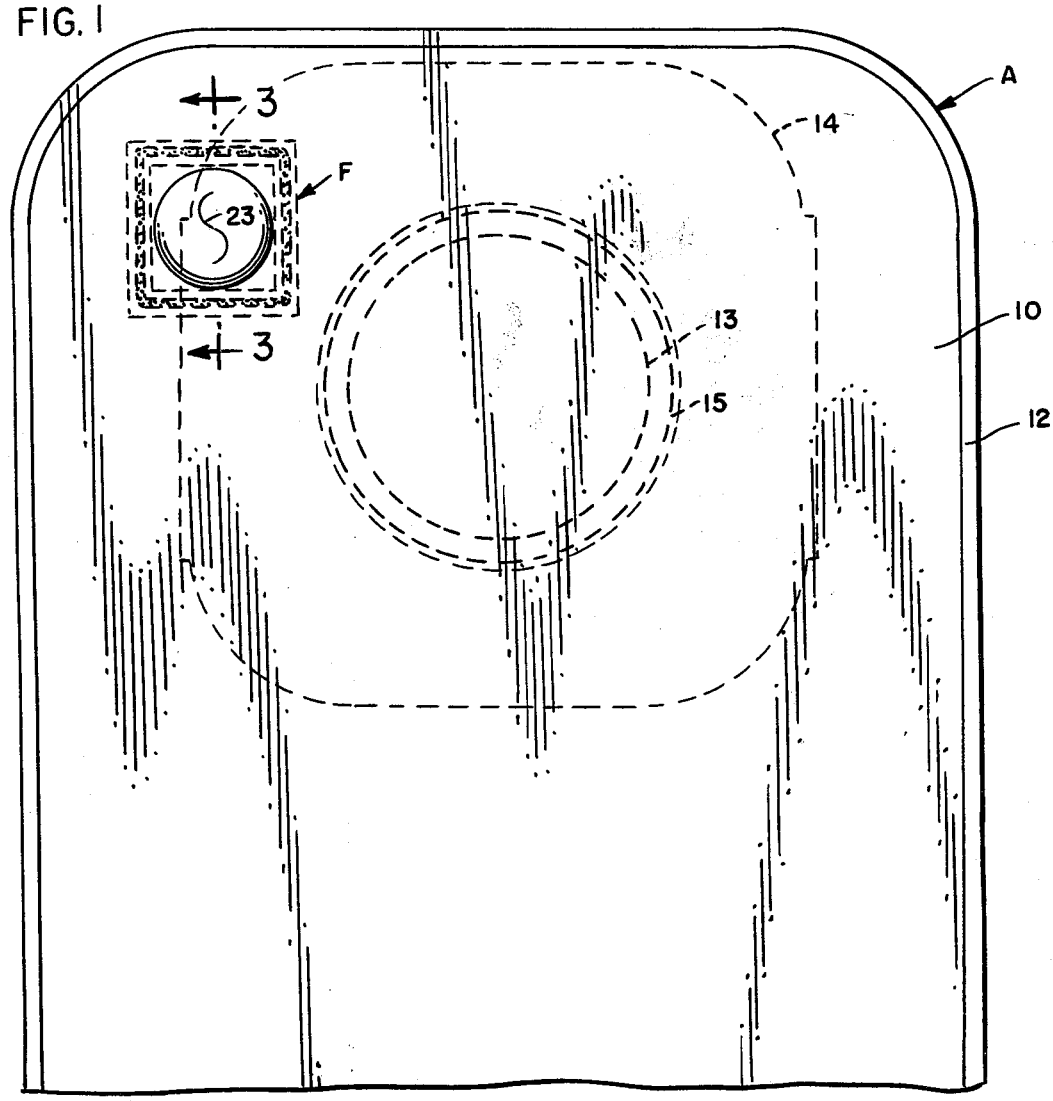
FIG. 1 is a front elevational view of a stoma pouch, such as a non-drainable colostomy bag, which is equipped with the filter assembly of the invention, part of the lower portion of the bag or pouch being broken away.

Looking first at FIG. 1, there is shown a collection appliance A, which in the illustration given is a stoma pouch, such as a non-drainable colostomy pouch. The envelope providing the pouch enclosure is formed from panels of fluid impermeable thermoplastic sheet material. The front panel 10 and the rear panel 11 (FIG. 3) are sealed together around their peripheries, such as by a heat seal bond 12. For example, the panels may be formed of barrier-coated polyethylene. A particularly suitable commercial material comprises low density polyethylene coextruded with a saran core. This material is commercially available under the trademark "Saranex" from Dow Chemical U.S.A., Midland, Mich. It will be understood, however, that other thermoplastic sheet materials can be used which are substantially impermeable to liquids and gases.

The rear panel 11 of the ostomy appliance A, in accordance with standard practice, is provided with a stomareceiving opening 13 (shown in dotted lines in FIG. 1). The outlet of the adhesive attachment patch 14 can also be seen in FIG. 1. In the illustration given, the patch 14 consists of a sheet of thermoplastic material which has an opening corresponding with opening 13 and which is heat sealed as indicated at 15 to the outside of rear panel 11 around the opening 13. From the heat seal, the patch 14 extends outwardly in separated relation to the rear panel. The rear surface of the patch 14 may be coated with a pressure-sensitive medical adhesive, so that after removal of the protective papers from the adhesive, the ostomy appliance may be mounted over the stoma. This adhesive attachment will provide a seal around the stoma so that the liquid or gas discharge will pass into the enclosure of the pouch.

Where the pouch has a substantial downward extent and is designed to retain larger amounts of discharge from the stoma, a relatively rigid gasket may be heat sealed to the rear panel of the pouch, being interposed between the adhesive patch 14 and the panel around the stoma opening. The gasket may be provided with belt attachment tabs for additional support of the stoma appliance, and a protective sealing composition may be applied to the gasket in the form of a ring, such as karaya, or mixtures of hydrocolloids with synthetic resins or elastomeric adhesives. It will be understood that patch 14 may be formed of breathable sheet material, such as a microporous non-woven sheet material. These details do not form a necessary part of the present invention, and since they are well known in the present commercial art of ostomy appliances, it will not be necessary to further describe them herein.

Turning now to the gas-venting filter assembly of this invention, it may be seen that the filter assembly F is located on the inside of the upper portion of the front panel 10. The assembly includes a recess 16 provided in the upper portion of front panel 10. As can be seen from FIG. 3, the portion 10a of the front panel which provides the recess 16 is displaced outwardly from the plane of the front panel. The depth of recess 16 is not critical, providing it is sufficient to maintain panel portion 10a normally free of tension and out of contact with the filter unit 17 which bridges the inside of recess 16. For example, the recess may have a depth of from about 2 to 4 mm. Since panel 10 is thermoplastic sheet material, the recess 16 can be readily formed by use of a heated die or mandrel.

As will be noted, the filter unit 17 is of generally flat or planar configuration. In the illustration given, it consists of a gas-porous cake 18 containing activated carbon as the gas adsorbent, and a rear or interior cover member 19 together with a front or outer cover member 20. Cover members 19 and 20 are formed from gas-porous sheet materials. The porosity of the elements comprising the filter unit 17 is such that gas from within the pouch enclosure can flow freely through the filter unit, as indicated by the arrows in FIG. 3.

Preferably, the inner cover 19 is formed of a gas-porous sheet material which is repellent to the liquid stoma discharge. Therefore, air-transmission and water-resistance are desirable characteristics of cover 19. The type of non-woven cellulosic sheet material used for operating room drapes or surgical gowns can be employed. For example, such air-porous liquid-repellent sheet material is sold under the trademark "Kaycel" by Kimberly-Clark Corp., Medical Fabrics Marketing Unit, Neenah, Wis. Although Kaycel or similar material can be assembled by heat sealing without additional coating, it has been found desirable to at least coat the outer or front peripheral portions of the covers 19 with a heat-sealable coating material. For example, a heat-sealable latex emulsion coating can be used, such as the coatings sold under the trademark "Latiseal", by Pierce & Stevens Chemical Corp., Buffalo, N.Y.

Front cover 20 may also be formed of an air-transmissable water-repellent sheet material such as the "Kaycel" material described above. However, to facilitate assembly of the filter unit, it has been found desirable to form member 20 of a non-woven synthetic fiber sheet material, such as spunbonded olefin sheet material. A suitable product of this type is sold under the trademark "Tyvek" by E. I. DuPont, Wilmington, Del. For example, Tyvek 1622E can be used. Such sheet material is inherently air-porous and additionally has a multiplicity of small perforations 21 therein. The arrows in FIG. 3, therefore, merely indicate the general direction of flow.

The gas-porous cake 18 of the filter unit preferably contains activated carbon as the deodorizing agent for the vented gas. It has been found that such deodorization can be obtained during the normal use period of a non-drainable colostomy pouch, even though the cake of filter material is relatively thin, and even though gas is permitted to flow freely through the filter unit. For example, the filter cake 18 may be formed of a mixture of paper fiber and activated carbon, the resulting material being a carbon-impregnated paper. Approximately equal amounts by weight of the paper fiber and the activated carbon may be used. Such carbon-impregnated paper can be prepared by standard paper making procedures. A high grade of activated carbon should be used for best results. For example, Type IVP Granular Activated Carbon can be used, as supplied by Calgon Corporation, Pittsburgh, Pa. Such activated carbon is specially prepared for use in vapor phase odor applications, and has high capacity for gases such as hydrogen sulfide and methyl mercaptan. With this type of activated carbon, and using a 50% impregnation ratio, cake 18 can perform satisfactorily even though its thickness is as small as 1 to 1.5 mm.

Preferably, the filter unit 17 is pre-assembled. The appearance of the pre-assembled unit is shown in FIGS. 5 and 6. The covers 19, 20 are heat-sealed around cake 18 as indicated at 22a. The recess 16 is also pre-formed in panel 10, as indicated in FIG. 6, which shows the filter unit 17 prior to attachment to front panel 10. The filter unit 17 is pressed against panel 10 and secured thereto by a second heat seal 22b (FIG. 3).

Figure 2:
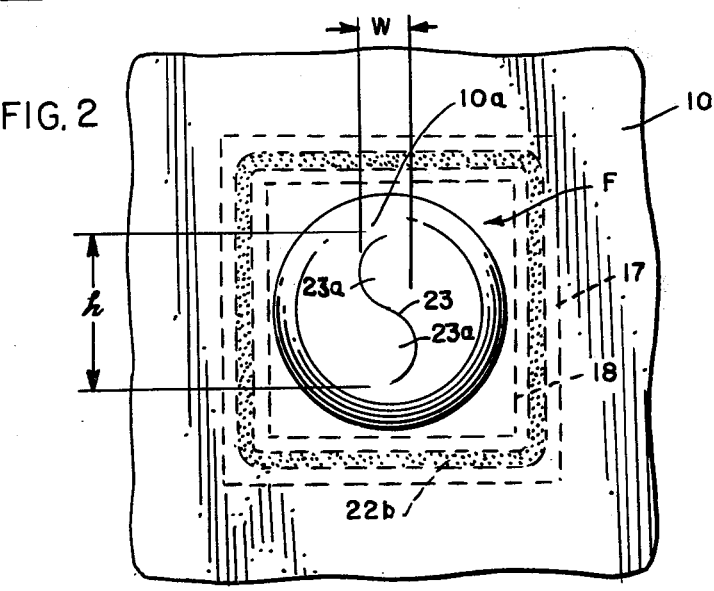
FIG. 2 is an enlarged fragmentary view of the filter assembly as seen from the front, corresponding to FIG. 1.

In accordance with the present invention, the panel portion 10a which forms a spaced cover over the outside of filter unit 17 is provided with gas outlet aperture means. For the purpose of the present invention, the aperture should be of a size and shape that renders it essentially non-flow-restricting with respect to the vented gas. For reasons which will subsequently be described in detail, it has been found particularly desirable to utilize a slit, such as the slit 23, as the aperture means. Preferably, the slit has a generally vertical or longitudinal orientation, as shown, with respect to the body of the pouch and has a generally S-shaped configuration as depicted in FIGS. 1 and 2. The slit aperture can be formed at the same time as the recess 16, the forming mandrel carrying or pressing the panel portion 10a against a slitter. A length of from 8 to 10 mm. is sufficient for slit 23. Correspondingly, recess 16 may be formed as a generally flat-topped circular dome having a diamter of around 20 mm.

After completion of the assembly of the appliance A, it is desirable to test the appliance for leaks. Such leakage may occur through defects in the films or in the heat seals 12, 15, 22a or 22b. Even very tiny leakage channels may permit some liquid or gas to escape from the appliance during usage, and this is objectionable to the wearer. It is therefore advantageous that the installation of the filter assembly of this invention does not interfere with leakage testing.

In carrying out the testing, an expandable rubber chuck may be applied to the opening 13, forming a seal therewith. Pressurizing air is then introduced into the enclosure of the pouch, as indicated in FIG. 4. In the area of the filter assembly, the front panel 10 of the bag is pressed against a holding member providing a pad P, the forward face of which engages panel portion 10a, thereby impeding the free escape of gas through the filter vent. As a result of such impariment of free gas flow through the vent, the pressure within the pouch increases to urge the edges of the slit tightly against pad P effecting a complete seal of the vent. Once that condition is achieved, a pressure gauge is used to monitor any pressure change within the pouch. If the pressure remains constant, the pouch passes the leakage inspection and is approved for commercial distribution.

In the use of the pouch, panel portion 10a is normally disposed in a generally flat untensioned state with the edges of slit 23 engaging each other to block entry of foreign material (including liquids) into the pouch. When even a slight increase in pressure develops within the pouch, the edges of the slit separate to permit the escape of filtered gas. The slit therefore performs a valving function in allowing the escape of gas while resisting the entry of foreign materials or liquids.

The S-shaped configuration of the slit is important because tensioning forces exerted in a direction longitudinal to the slit (i.e., vertical) promote rather than reduce the opening of the slit and because such a slit tends to be selfclosing in the absence of a pressure differential. Referring to FIG. 2, it will be observed that the shallow S-shaped slit defines a pair of arcuate flaps 23a which face in opposite directions, each flap serving as a flexible closure element. The width w of the vertically-oriented S-shaped slit should be not more than about one half, nor less than about one fifth, of the height h of the slit. Because of the flexible nature of the thermoplastic material from which panel 10 is formed, the generally planar configuration of the displaced portion 10a (when that portion is untensioned), and the shallow (i.e., relatively narrow) configuration of the S-shaped slit, flap portions 23a readily return to their closed or sealing positions in the absence of a pressure differential.

It is believed that other aperture or slit configurations may be used but would be less effective than the S-shaped configuration shown in FIGS. 1 and 2. For example, a relatively straight slit may be provided but such a vent configuration has the disadvantage or presenting a slight but noticeable resistance to opening in the presence of tensioning forces extending longitudinally with respect to the slit. Other types of apertures, although performing a venting function, may lack the self-closing feature and therefore be less effective in performing a protective function.

As indicated, panel portion 10a serves as a protective cover for the outside of the filter, shielding it from the clothing of the wearer, or from coming into contact with substances which could reduce the porosity of the filter, such as adhesives or skin protective gels that may be used with collection appliances. Further, if the ostomate desires to wear the appliance in a shower, the protective cover 10a provides a deflector action for the shower water. In that connection, it has been found that the vertical alignment of the slit aperture is more desirable than a horizontal orientation since the latter might have a greater tendency to trap water within the recess 16.

While in the foregoing we have disclosed an embodiment of the invention in considerable detail for purposes of ilustration, it will be understood by those skilled in the art that many of these details may be varied without departing from the spirit and scope of the invention.

We claim:

1. In combination with a collection appliance formed of fluid and odor impermeable thermoplastic sheet material, said appliance including panels defining an enclosure and having an opening therein for receiving body discharge, and attachment means for forming a temporary seal about said opening so that body discharge passes into said enclosure, a gas-venting filter assembly comprising:

(a) a recess provided in one of said panels, the portion of said one panel providing said recess being displaced outwardly from the plane of said one panel;

(b) a generally planar filter unit bridging said recess with its peripheral portion sealed to said one panel around said recess; and (c) gas outlet aperture means formed in said outwardly displaced panel portion, said aperture means being of sufficient size so as to be essentially non-flow restricting with respect to the vented gas, and said outwardly displaced panel portion in which said gas outlet aperture means is formed being normally spaced from said filter unit.

2. The combination of claim 1 in which said filter unit comprises a gas-porous cake containing activated carbon covered on its opposite sides by gas-porous sheet material so that gas from within said enclosure can flow freely through said filter unit.

3. The combination of claim 2 in which said gas-porous sheet material enclosing at least one of the sides of said cake is repellant to liquid discharge.

4. The combination of claim 1 in which said gas outlet aperture means consists of a slit in said outwardly displaced panel portion.

5. The combination of claim 4 in which said slit is oriented generally vertically when said appliance is worn.

6. The combination of claim 4 in which said slit has a shallow and vertically oriented S-shaped configuration.

7. The combination of claim 6 in which said S-shaped slit has a width no greater than one half and no less than one fifth of the height thereof.

8. The combination of claims 4, 5, 6, or 7 in which said displaced panel portion is generally planar when the same is in an untensioned and unflexed state.

9. In combination with a collection appliance formed of fluid and odor impermeable thermoplastic sheet material, said appliance including flexible panels defining an expandable enclosure and having an opening therein for receiving body discharge, and attachment means for forming a temporary seal about said opening so that body discharge passes into said enclosure, a gas-venting filter assembly comprising:

(a) a recess provided in one of said panels, the portion of said one panel providing said recess being generally planar when in an untensioned state and being displaced outwardly from the plane of said one panel;

(b) a generally planar filter unit bridging said recess and normally being spaced from said outwardly displaced panel portion, said filter unit having its peripheral portion sealed to said one panel around said recess; and (c) gas outlet aperture means consisting of a slit formed in said outwardly displaced panel portion, said slit being of sufficient size so as to be essentially non flow restricting with respect to vented gas.

10. The combination of claim 9 in which said filter unit comprises a gas-porous cake containing activated carbon covered on its opposite sides by gas-porous sheet material so that gas from within said enclosure can flow freely through said filter unit.

11. The combination of claim 10 in which said gas-porous sheet material enclosing at least one of the sides of said cake is repellent to liquid discharge.

12. The combination of claim 9 in which said slit is S-shaped in configuration.

13. The combinaton of claim 12 in which said S-shaped slit has a width no greater than one half and no less than one fifth of the height thereof.

14. The combination of claims 9, 10, 11, 12 or 13 in which said slit is oriented generally vertically when said appliance is positioned for wear.

* * * * *